US012140656B2

(12) United States Patent
Rausch et al.

(10) Patent No.: US 12,140,656 B2
(45) Date of Patent: Nov. 12, 2024

(54) METHOD FOR PRODUCING A LIGHT-CURABLE RESIN COMPOSITION

(71) Applicant: MEDIZINISCHE UNIVERSITÄT WIEN, Vienna (AT)

(72) Inventors: Ivo Rausch, Vienna (AT); Alejandra Valladares, Vienna (AT); Ewald Unger, Vienna (AT); Andreas Berg, Deutsch-Wagram (AT); Peter Rosenbüchler, Vienna (AT)

(73) Assignee: MEDIZINISCHE UNIVERSITÄT WIEN, Vienna (AT)

( * ) Notice: Subject to any disclaimer, the term of this patent is extended or adjusted under 35 U.S.C. 154(b) by 124 days.

(21) Appl. No.: 18/026,740

(22) PCT Filed: Sep. 15, 2021

(86) PCT No.: PCT/IB2021/058405
§ 371 (c)(1),
(2) Date: Mar. 16, 2023

(87) PCT Pub. No.: WO2022/064324
PCT Pub. Date: Mar. 31, 2022

(65) Prior Publication Data
US 2023/0341495 A1 Oct. 26, 2023

(30) Foreign Application Priority Data
Sep. 23, 2020 (EP) ..................................... 20020427

(51) Int. Cl.
*G01R 33/58* (2006.01)
*B33Y 10/00* (2015.01)
(Continued)

(52) U.S. Cl.
CPC .............. *G01R 33/58* (2013.01); *B33Y 10/00* (2014.12); *B33Y 70/00* (2014.12); *B33Y 80/00* (2014.12);
(Continued)

(58) Field of Classification Search
CPC ...... G01R 33/58; G01R 33/481; B33Y 10/00; B33Y 70/00; B33Y 80/00; B33Y 70/10;
(Continued)

(56) References Cited

U.S. PATENT DOCUMENTS

2007/0164739 A1   7/2007   Clarke et al.
2012/0308708 A1*  12/2012  Seibold .................... A23D 7/04
                                                                426/549

FOREIGN PATENT DOCUMENTS

EP      3671344 A1     6/2020
WO      2010115145 A2  10/2010
WO      2016007939 A1  1/2016

OTHER PUBLICATIONS

International Search Report and Written Opinion received in PCT/IB2021/058405 dated Dec. 14, 2021, pp. 10.
(Continued)

*Primary Examiner* — G. M. A Hyder
(74) *Attorney, Agent, or Firm* — Liang & Hennessey LLP; Brian Hennessey

(57) ABSTRACT

Method for producing a light-curable resin composition capable of producing a magnetic resonance imaging-signal, in particular for the lithography-based additive production of magnetic resonance imaging phantoms, the method comprising at least the following steps: providing particles at least partially filled with a magnetic resonance imaging-signal producing liquid, and mixing the at least partially filled particles with a light-curable resin.

15 Claims, 3 Drawing Sheets

Materials and manufacturing process of the samples.

(51) Int. Cl.
    *B33Y 70/00*     (2020.01)
    *B33Y 80/00*     (2015.01)
    *C08J 3/20*     (2006.01)
    *C08K 7/16*     (2006.01)
    *C08K 9/10*     (2006.01)

(52) U.S. Cl.
    CPC ............... *C08J 3/20* (2013.01); *C08K 7/16* (2013.01); *C08K 9/10* (2013.01); *C08J 2333/08* (2013.01); *C08K 2201/003* (2013.01); *C08K 2201/006* (2013.01)

(58) Field of Classification Search
    CPC ........... C08J 3/20; C08J 2333/08; C08K 7/16; C08K 9/10; C08K 2201/003; C08K 2201/006; B29C 64/124; G03F 7/027; G03F 7/038; G03F 7/0037; A61B 6/583
    See application file for complete search history.

(56) References Cited

OTHER PUBLICATIONS

Mitsouras et al., "Three-Dimensional Printing of MRI-Visible Phantoms and MR Image-Guided Therapy Simulation", Magnetic Resonance in Medicine, 2016, pp. 21.

\* cited by examiner

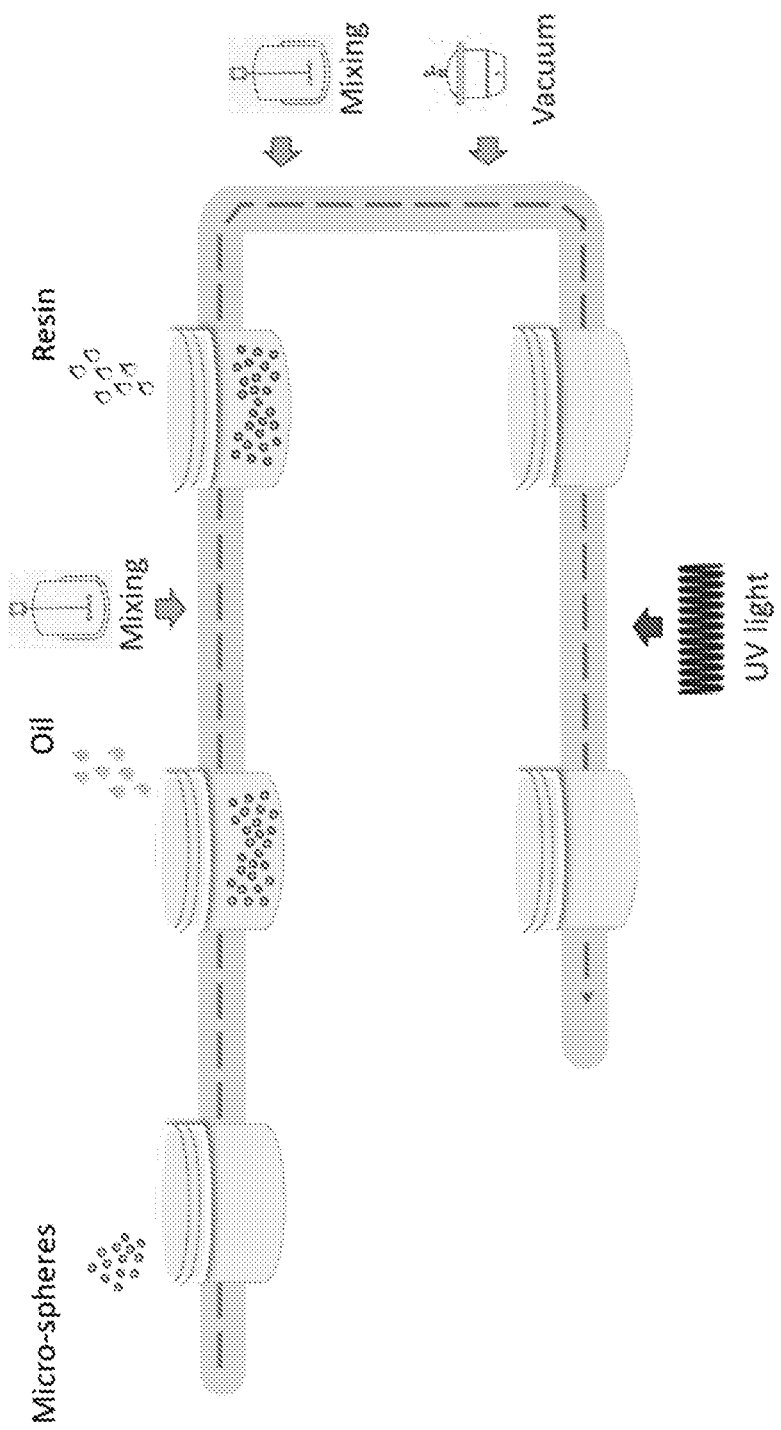
Figure 1. Materials and manufacturing process of the samples.

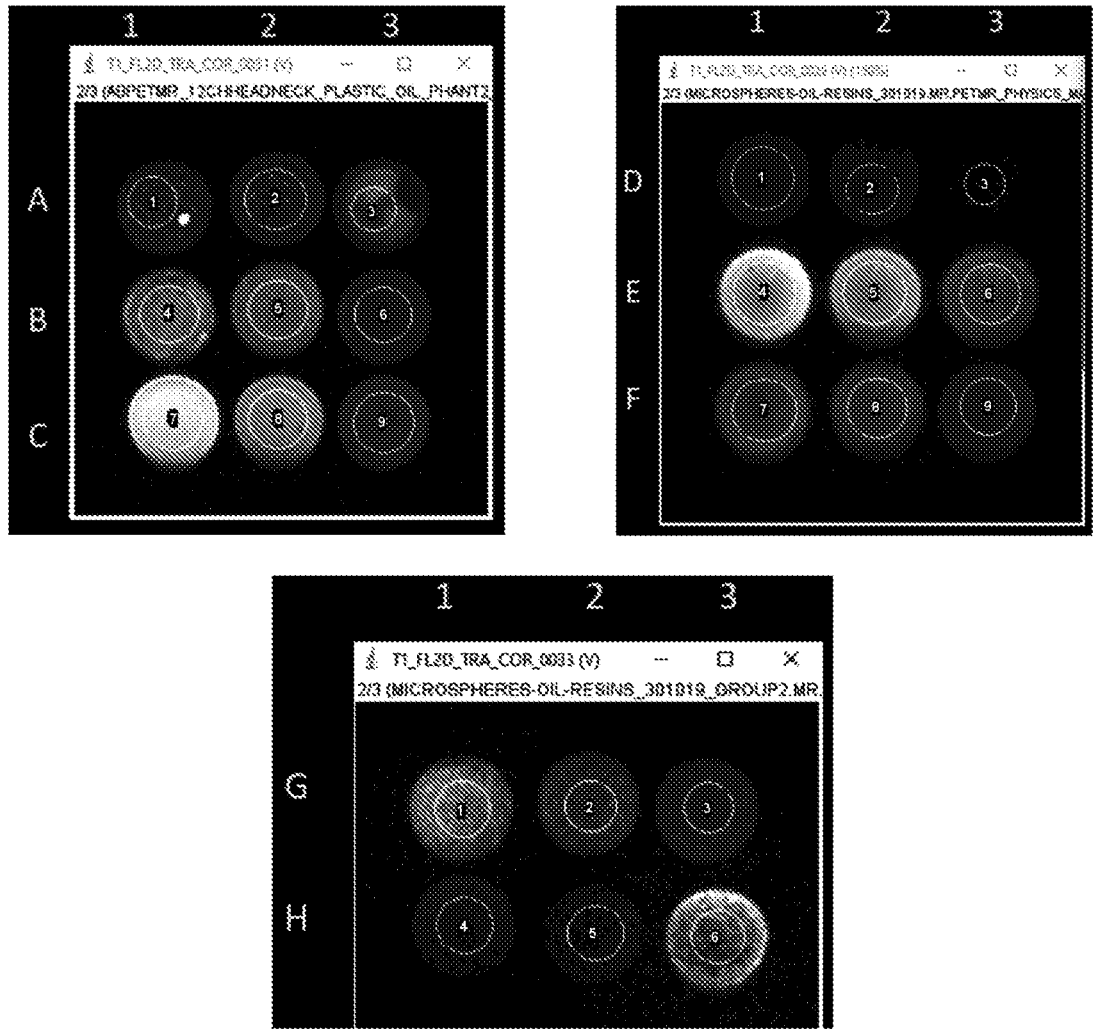
Figure 2. HR MR images of the probes.

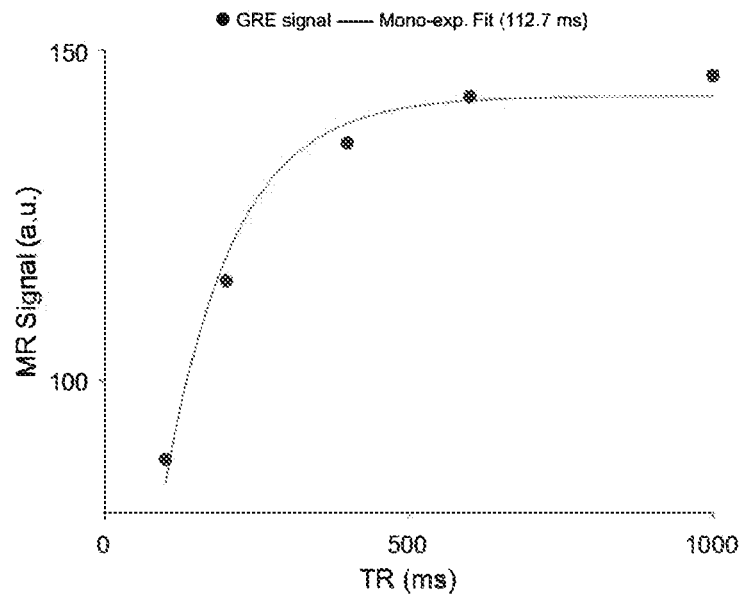
Fig. 3a - Gradient echo signal and T1 fitting for sample E1
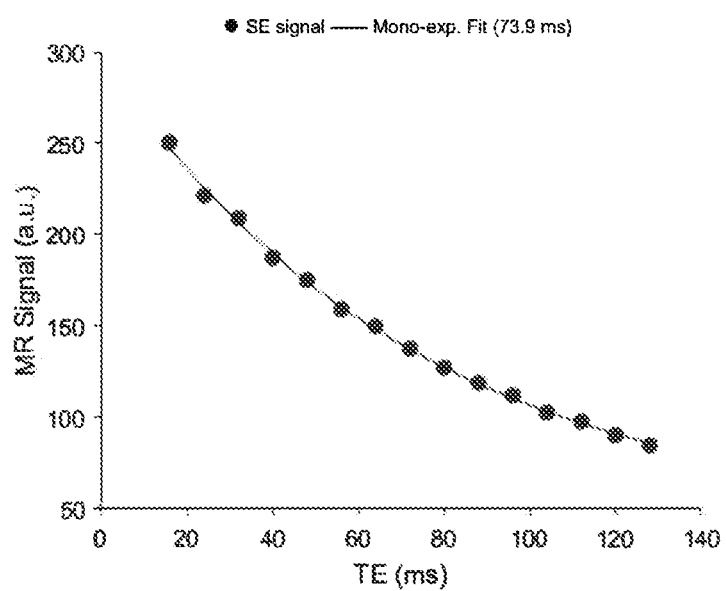
Fig. 3b - Single-echo spin-echo signal with T2 fitting for the same sample

METHOD FOR PRODUCING A LIGHT-CURABLE RESIN COMPOSITION

CROSS-REFERENCE TO RELATED APPLICATIONS

The present application is a national phase application of PCT Application No. PCT/IB2021/058405, filed Sep. 15, 2021, entitled "METHOD FOR PRODUCING A LIGHT-CURABLE RESIN COMPOSITION", which claims the benefit of European Patent Application No. 20020427.9, filed Sep. 23, 2020, each of which is incorporated by reference in its entirety.

BACKGROUND OF THE INVENTION

1. Field of the Invention

The present invention is directed to a method for producing a light-curable resin composition capable of producing a magnetic resonance imaging-signal. Further, the invention relates to a magnetic resonance imaging-signal producing, light-curable resin composition as well as a magnetic resonance imaging phantom.

2. Description of the Related Art

In diagnostic medical imaging the performance of imaging modalities of magnetic resonance imaging (MRI) systems needs to be tested and evaluated on a regular basis in order to ensure the correct functioning of the hardware and software used in the imaging system and method. For this purpose, physical imaging phantoms are produced and subjected to the specific imaging method to obtain comparative data on the imaging performance of the system. These phantoms sometimes have simple geometric shapes but may also be manufactured to mimic complex anatomical structures of the body region or organ to be visualized by the imaging method. Up to now, phantoms of complex shapes are mostly built from acrylic resin plates forming cavities in the shape of anatomical body structures and the cavities are filled with water or other proton-rich fluids such as lipids in varying concentrations to obtain the imaging data. Based on this data, the imaging system is adjusted to give reasonable and comparable imaging of real body parts or body regions of a patient.

Physical imaging phantoms for quality control and research in the field of Positron Emission Tomography (PET) are mostly composed of PMMA (polymethylmethacrylate) or the like. In the context of PET/MRI (magnetic resonance imaging) hybrid imaging, the use of these materials leads to a problem related with attenuation correction since the PMMA is not visible in MRT. The current solution is the use of a CT scan to generate attenuation correction maps of the phantoms used in PET/MR.

The ever-improving capabilities of 3D printing technology has fostered the interest in producing physical imaging phantoms by 3D printing and in particular by a technique referred to as lithography-based photopolymerization. This technique involves applying a layer of photopolymerizable resin on a light transmissive plate and lowering a build platform into the resin until a desired layer thickness between the plate and the platform is achieved. Then, the layer is location-selectively irradiated with light to cure the resin in the irradiated regions of the layer according to a layered 3D model of an organ or body region. After this first step, the platform is raised, together with the first cured layer, the resin layer is replenished and the platform with the first layer is subsequently lowered into the resin to form the next layer according to the layered 3D model of the organ or body region. This process is repeated until all the layers of the 3D model have been cured and the object, in this case the phantom of a body region or an organ, is completed.

SUMMARY OF THE INVENTION

It is an object of the present invention to allow 3D printing of physical imaging phantoms for magnetic resonance imaging.

To this end a method for producing a light-curable resin composition capable of producing a magnetic resonance imaging-signal, in particular for three-dimensional lithography-based additive production of magnetic resonance imaging phantoms is provided, the method comprising at least the following steps:

providing particles, in particular spherical particles, at least partially filled with a magnetic resonance imaging-signal producing liquid, mixing the at least partially filled particles with a light-curable resin.

By this inventive method it becomes feasible to include a magnetic resonance imaging (MRI)-signal producing material in a light-curable resin so that the resin composition can be used in 3D-lithography. The particles are filled with an MRI-signal producing liquid and keep it within the mixture with the light curable resin. Without the use of such particles, the MRI-signal producing liquid would segregate from the light-curable resin.

Preferably, the particles are provided as porous particles, in particular porous spherical particles, and are mixed with the magnetic resonance imaging-signal producing liquid thereby obtaining particles at least partially filled with the liquid, the pores of the particles preferably having an arithmetic mean diameter of 150-250 Å, more preferably of 180-220 Å. Such porous particles absorb the MRI-signal producing liquid so as to allow for the stable integration of high concentrations of the MRI-signal producing liquid into the light-curable resin.

According to a preferred alternative of the present invention, the particles are provided as hollow particles, in particular hollow spherical particles, that are filled at least partially with a magnetic resonance imaging-signal producing liquid. Hollow particles within the sense of the present invention are particles with a continuous shell enclosing a void therein. In the void inside such hollow particles, the magnetic resonance imaging-signal producing liquid is safely encapsulated.

According to a preferred embodiment of the invention, the particles are made of an acrylic resin, preferably a cross-linked polymethylmethacrylate.

Preferably, the spherical particles, in particular the cross-linked polymethylmethacrylate spherical particles, have an arithmetic mean diameter of 5 µm to 50 µm, preferably 10 µm to 40 µm, more preferably 20 µm to 30 µm and most preferably 25 µm, and may therefore be referred to as micro-particles. Using micro-particles results in that their size does not interfere with the thickness of the material layers used in the 3D printing process to build a phantom in a layer-by layer process. The claimed mean diameters are small enough to build physical layer phantoms with a sufficiently high resolution of the various anatomical structures to be mimicked. As already described, when the particles are provided as porous particles, the pores of the particles preferably have a mean diameter of 150-250 Å, more preferably of 180-220 Å. Also, in this case, the porosity of the porous particles is of the open porosity-type. This means that the pores within the particles mostly communicate with each other and mostly do not form closed cavities.

The inventive method is preferably carried out in such a manner that the particles are filled with magnetic resonance imaging-signal producing liquid to 25 wt.-% to 75 wt.-%, preferably 35 wt.-% to 65 wt.-%, more preferably 45 wt.-% to 55 wt.-%, most preferably 50 wt.-% of the total absorption capacity of the particles. A preferred embodiment provides that the particles have an oil absorption capacity of 100-180 ml/100 gr, preferably 120-160 ml/100 gr. Micro-particles having an absorption capacity in this range are available on the market (e.g. Techpolymer MBP-8 available from Sekisui Kasei Co., Ltd.). The at least partial filling of the pores of porous particles with the magnetic resonance imaging-signal producing liquid may result in an absorption of e.g. between 35 ml and 105 ml of the liquid per 100 g of particles. By varying the filling ratio of the particles, the signal from the imaging system and thus the image obtained can be adjusted and, therefore, more realistic phantoms can be produced. In particular, the filling degree of the particles allows to adjust the signal intensities and the relaxation times to be obtained when using the MRI phantom. The adjustability of the MRI contrast parameters as e.g. T1 (see Table 3) is advantageous for the production of phantoms which give an MR-imaging appearance that is similar to that of different heterogeneous human tissue and organs. These phantoms are comparably stable with time and allow for the optimization of measurement protocols and data processing without using patients or subjects.

According to a preferred embodiment of the invention, the particles, in particular the spherical particles, have a specific surface area of 60-100 $m^2/g$, preferably 80-90 $m^2/g$.

As to the pores of the porous particles, any configuration of pores is possible within the scope of the invention, as long as an open porosity is ascertained. According to a preferred embodiment, the pores of the particles may have a mean diameter 150-250 Å, preferably 180-220 Å.

Any MRI-visible substance may be used as the MRI-signal producing liquid, in particular water or a lipid. Preferably, a triglyceride is used as said magnetic resonance imaging-signal producing liquid. Preferably, the magnetic resonance imaging signal producing liquid is selected from one or more of the group comprised of seed oil, sunflower oil, paraffin oil and silicon oil. Sunflower oil and paraffin oil are preferred. The magnetic resonance imaging signal producing liquid can be chosen differently for different regions of the phantom to be produced and, thus, phantoms more realistically responding to the imaging system can be obtained.

In the context of the present invention, another approach to achieve 3D-printed phantoms having regions with different response in the imaging system, mimicking anatomical structures such as organs, bones, tendons and the like, is to vary the portion of the particles at least partially filled with the liquid with regard to the resin, into which the particles are mixed. It is, therefore, preferred that the amounts of particles at least partially filled with the liquid and of the light-curable resin are chosen so as to obtain a weight ratio of 3:10-10:10, preferably 4:10-6:10.

In order to eliminate bubbles and voids in the resin composition according to the present invention, the method preferably further comprises the step of subjecting the mixture of the at least partially filled particles with the light-curable resin to a vacuum.

Preferably, the light-curable resin used in the method of the invention is a photopolymer resin, such as an acrylic resin.

According to a further aspect, the invention refers to a magnetic resonance imaging-signal producing, light-curable resin composition comprising a mixture of a light-curable resin with particles that are at least partially filled with a magnetic resonance imaging-signal producing liquid.

Preferred features of said light-curable resin composition have been described in the context of the method of the invention and may be equally applied to the light-curable composition.

According to a further aspect, the invention refers to a method of producing a magnetic resonance imaging phantom, comprising the steps of:
  providing a mixture of a light-curable resin with particles that are at least partially filled with a magnetic resonance imaging-signal producing liquid, in particular produced by a method according to the present technology,
  building the phantom layer-by-layer by means of an additive manufacturing process, comprising:
    a) applying a layer of the mixture on a material carrier or on the partly built phantom,
    b) exposing the layer to an electromagnetic radiation in order to position-selectively cure said layer according to a desired layer geometry,
    c) repeating steps a) and b) until the phantom is complete.

BRIEF DESCRIPTION OF THE DRAWINGS

In the following, the invention will be described in more detail with reference to the following examples and the figures. In the figures, FIG. 1 schematically illustrates a method of producing a light-curable resin composition, FIG. 2 shows MR images of some probes and FIG. 3 presents relaxation rate curves and the curve fittings for T1-w and T2-w images.

DETAILED DESCRIPTION

The inventive method was tested by producing solid probes from the light-curable resin composition obtained by the method according to the present invention.

24 probes (diameter=50 mm, height=9 mm) were created by using porous, cross-linked polymethylmethacrylate spherical particles (microspheres) (Techpolymer MBP-8), Formlabs Standard Photopolymer Clear photopolymer resin and different oil types (i.e. Silicon oil EBESIL 100, conventional sunflower oil, standard paraffin oil and Silicon oil AK 0.65). The concentration of oil varied between 25%-75% with respect to the oil absorption capacity of the microspheres for seed oil (140 mL/100 g).

The preparation of the probes was divided into two experiments. For the first one, Silicon EBESIL 100, sunflower and paraffin oil were used separately to build the probes. For the second experiment, the order of mixing the microspheres with a specific oil type was changed to evaluate the time influence on a presumable separation of the oil from the microspheres. Another silicon oil with less viscosity than the previous one (silicon AK 0.65) was additionally used. For each experiment, the preparation was as shown in FIG. 1.

As schematically illustrated in FIG. 1, 4 g of Techpolymer porous, cross-linked polymethylmethacrylate spherical particles were first weighted in a separated plastic container (diameter=50 mm, height=50 mm). Second, the corresponding type and amount of oil was added to the microspheres and mixed manually. Third, 10 mL (roughly 10 g) of Formlabs resin was added to each probe and mixed manually. Once the mixtures were prepared, the probes were placed in a vacuum machine to remove the air bubbles generated during the previous manufacturing process. Finally, to cure the resin and therefore, to obtain the solid probes, the samples were exposed to UV light (roughly 400V) during 105 minutes. Labeling of the probes and details of the concentrations of the components are shown in Table 1.

TABLE 1

Samples labeling and component percentages

| Exp # | Oil type | Label | Oil amount (%) | Oil amount (mL) |
|---|---|---|---|---|
| 1 | Silicon - EBESIL 100 | A1 | 75 | 3 |
|  |  | A2 | 50 | 2 |
|  |  | A3 | 25 | 1 |
|  | Sunflower | B1 | 75 | 3 |
|  |  | B2 | 50 | 2 |
|  |  | B3 | 25 | 1 |
|  | Parafine | C1 | 75 | 3 |
|  |  | C2 | 50 | 2 |
|  |  | C3 | 25 | 1 |
| 2 | Silicon - AK 0.65 | D1 | 75 | 3 |
|  |  | D2 | 50 | 2 |
|  |  | D3 | 25 | 1 |
|  | Parafine | E1 | 75 | 3 |
|  |  | E2 | 50 | 2 |
|  |  | E3 | 25 | 1 |
|  | Sunflower | F1 | 75 | 3 |
|  |  | F2 | 50 | 2 |
|  |  | F3 | 25 | 1 |
|  | Silicon - EBESIL 100 | G1 | 75 | 3 |
|  |  | G2 | 50 | 2 |
|  |  | G3 | 25 | 1 |
|  | Silicon - AK 0.65 | H1 | 75 | 3 |
|  |  | H2 | 50 | 2 |
|  |  | H3 | 25 | 1 |

Relaxation rates measurements were performed on a 3T Siemens Biograph mMR PET/MR system with an mMR Head/Neck Matrix coil, 12-elements design (Tim coils).

The sequences and parameters used are presented in Table 2. T1-weighted images were obtained with a 2D-GR sequence for 5 repetition times (TR), from 100 to 1000 ms.

TABLE 2

Pulse sequences and their parameters for relaxometry experiments. Measurements were performed on a Biograph mMR PET/MRI system with a body coil.

|  | Sequence | Flip Angle (°) | matrix | Slice thickness/spacing (mm) | TE (ms) [#echoes/echo spacing (ms)] | TR (ms) | Pixel BW (Hz/px) | NEX |
|---|---|---|---|---|---|---|---|---|
| T1 | 2D GR SP\OSP | 90 | 256 × 256 | 3/3.9 | 2.3 | 100 – 1000$^\Delta$ | 385 | 2 |
| T2 | 2D single-echo SP | 180 | 256 × 256 | 3/6 | 8-128 [16/8] | 3000 | 400 | 1 |
| HR | 2D GR SS | 70 | 320 × 320 | 3/6 | 2.3 | 50 | 380 | 32 |

For T2 measurements, a 2D single-echo sequence was used to acquire 16 echoes with 8 ms (milliseconds) spacing between each other. Finally, T1-w High Resolution images were acquired with a 2D-GR sequence (TR=50 ms, TE=2.3 ms, flip angle=70°, NEX=32).

One circular ROI (Region of Interest) was drawn on each visible probe in the MM images for each sequence used. Mean values and standard deviation of the ROIs were extracted to calculate the relaxation rates and homogeneity for each experiment.

The R1 (R1=1/T1) was estimated using the equation $$s(t)=k(1-e^{-tR_1}),$$

where k is a constant and t the repetition time. As suggested in previous works (Milford, D.; Rosbach, N.; Bendszus, M.; Heiland, S. Mono-Exponential Fitting in T2-Relaxometry: Relevance of Offset and First Echo. PLoS ONE 2015, 10, e0145255) R2 rates (R2=1/T2) were obtained fitting the data (excluding the first echo time=8 ms) to the mono-exponential model $$s(t)=\alpha e^{-tR_2}+\beta,$$

where α is an MM-related constant and t the echo time. Curve fittings were performed in MATLAB R2016a implementing optimised iterative nonlinear routines. Finally, to assess homogeneity of the samples, coefficient of variation (StdDev/mean) were calculated from the ROI (Region of Interest) values of the HR (high resolution) images.

Results

For most of the probes, measurable signal intensities were obtained when using the sequences described in the previous section (see FIG. 2). FIG. 3 presents examples of the relaxation rates curves and the curve fittings for T1-w and T2-w images. Obtained T1-, T2- and homogeneity-values of the samples are shown in Table 3.

TABLE 3

Relaxation times for the built probes.

| Label | Relaxation times (ms) T1 | T2 | Homogeneity % CoV | Label | Relaxation times (ms) T1 | T2 | Homogeneity % CoV |
|---|---|---|---|---|---|---|---|
| A1 | 420.2 | 129.1 | 29.72 | G1 | N.M. | N.M. | 13.85 |
| A2 | 280.3 | 101.9 | 37.49 | G2 | N.M. | N.M. | 17.84 |
| A3 | 127.9 | 25.9 | 28.40 | G3 | N.M. | N.M. | 19.05 |
| B1 | 152.9 | 68.4 | 7.42 | F1 | 161.6 | 70.3 | 11.90 |
| B2 | 154.5 | 67.1 | 5.11 | F2 | 137.4 | 65.6 | 4.41 |
| B3 | 149.3 | 61.2 | 11.84 | F3 | 142.0 | 62.7 | 6.49 |
| C1 | 101.7 | 80.3 | 4.83 | E1 | 112.7 | 73.9 | 11.20 |
| C2 | 101 | 73.9 | 5.14 | E2 | 109.6 | 75.2 | 8.21 |
| C3 | 93.1 | 67.9 | 7.39 | E3 | 110.9 | 74.7 | 11.77 |
| D1 | 142 | N.M. | 9.94 | H1 | N.M. | N.M. | 46.32 |
| D2 | N.M. | N.M. | 22.76 | H2 | N.M. | N.M. | 72.51 |
| D3 | N.M. | N.M. | 33.86 | H3 | N.M. | N.M. | 33.51 |

N.M.: Not measurable

For some of the samples (D1-D3), the signal intensity was significantly low, hampering the quantification of the desired parameters. For samples G1-G3 and H1-H3, wrong connection of the coil led to similar quantification problems. For most of the visible samples, relaxation times presented differences below 5% across experiments for the same oil type and concentration. Only between samples B2-F2, C1-E1 and C3-E3, differences in T1 values were 5.86%, 5.13% and 8.73%, respectively. Finally, slight changes in homogeneity were observed between probes built with the same oil.

DISCUSSION AND CONCLUSION 24 solid probes were obtained by mixing acrylic microspheres with oil and 3D printing resin. T1 and T2 relaxation times as well as homogeneity of the visible probes were obtained from 3T MRI measurements. Differences in relaxation times between probes built with the same oil type and concentration were below 10% in all the cases.

Changes on homogeneity for samples built with the same components can be partly explained due to the manual mixing process, thus, suggesting a better control or automation of this step.

Likewise, although quantification on samples G1-G3 was not possible, visual observation of the MRI images suggests that the mixing process and preparation time influence on the characteristics of the material, at least when using high viscosity silicone oil. As can be observed, samples G1-G3 look more homogeneous than probes A1-A3 of the first experiment.

Based on the results, samples built with a 50% concentration of sunflower or paraffin oil (B2, F2, C2 and E2) seem to be the most promising in terms of compromise between relaxation times and homogeneity. Mixtures with the high viscosity silicon oil could also be considered if the time between the mixture of the components and the curing of the sample is short enough to reduce the effects of separation of the components.

Although the magnetic resonance imaging-signal producing, light-curable resin composition of the invention has been described in relation to the production of MRI-phantoms, the composition can also be used to produce devices other than phantoms. The composition may be produced for any object, for which MRI visibility is beneficial. This includes MM visible positioning aids in PET/MRI and radio therapy applications. The MRI visibility allows to calculate the attenuation of e.g. PET radiation by the phantom material based on MR-imaging data only without the necessity for additional x-ray or CT imaging.

The invention claimed is:

1. A method for producing a light-curable resin composition capable of producing a magnetic resonance imaging-signal, the method comprising:
   providing particles at least partially filled with a magnetic resonance imaging-signal producing liquid; and
   mixing the at least partially filled particles with a light-curable resin.

2. The method according to claim 1, wherein the particles are provided as porous particles and are mixed with a magnetic resonance imaging-signal producing liquid thereby obtaining particles at least partially filled with the liquid.

3. The method according to claim 1, wherein the particles are provided as hollow particles that are filled at least partially with a magnetic resonance imaging-signal producing liquid.

4. The method according to claim 1, wherein the particles are made of an acrylic resin.

5. The method according to claim 1, wherein the spherical particles have a mean diameter of 5 μm to 50 μm.

6. The method according to claim 1, wherein the particles are filled to 25 wt.-% to 75 wt.-% of the total absorption capacity of the particles.

7. The method according to claim 1, wherein the particles have an oil absorption capacity of 100-180 ml/100 gr.

8. The method according to claim 1, wherein the particles have a specific surface area of 60-100 $m^2/g$.

9. The method according to claim 1, wherein water or a lipid, in particular a triglyceride is used as said magnetic resonance imaging-signal producing liquid, wherein the magnetic resonance imaging-signal producing liquid is preferably selected from one or more of the group comprised of seed oil, sunflower oil, paraffin oil and silicon oil.

10. The method according to claim 1, wherein the amounts of particles at least partially filled with the liquid and of the light-curable resin are chosen so as to obtain a weight ratio of 3:10-10:10.

11. The method according to claim 1, further comprising the step of subjecting the mixture of the at least partially filled particles with the light-curable resin to a vacuum.

12. A magnetic resonance imaging-signal producing, light-curable resin composition obtained by a method according to claim 1.

13. A magnetic resonance imaging-signal producing, light-curable resin composition comprising a mixture of a light-curable resin with particles that are at least partially filled with a magnetic resonance imaging-signal producing liquid.

14. A magnetic resonance imaging phantom produced by curing a magnetic resonance imaging-signal producing, light-curable resin composition according to claim 13.

15. A method of producing a magnetic resonance imaging phantom, comprising the steps of:
- providing a mixture of a light-curable resin with particles that are at least partially filled with a magnetic resonance imaging-signal producing liquid, in particular produced by a method according to claim 1; and
- building the phantom layer-by-layer by means of an additive manufacturing process, the additive manufacturing process comprising:
  - a) applying a layer of the mixture on a material carrier or on the partly built phantom,
  - b) exposing the layer to an electromagnetic radiation in order to position-selectively cure said layer according to a desired layer geometry, and
  - c) repeating steps a) and b) until the phantom is complete.

\* \* \* \* \*